United States Patent [19]

Ho et al.

[11] 4,384,045
[45] May 17, 1983

[54] ACTIVATION OF A SILICEOUS CARRIER FOR ENZYME IMMOBILIZATION

[75] Inventors: Guan-Huei Ho; Chiang-Chang Liao, both of Tillsonburg, Canada

[73] Assignee: Borden, Inc., Columbus, Ohio

[21] Appl. No.: 179,915

[22] Filed: Aug. 20, 1980

[30] Foreign Application Priority Data

May 21, 1980 [CA] Canada ................................. 352341

[51] Int. Cl.³ ...................... C12N 11/14; C12N 11/18; C12N 11/06
[52] U.S. Cl. ................................... 435/176; 252/413; 252/449; 435/175; 435/181
[58] Field of Search ............... 435/176, 177, 180, 181; 252/449, 450, 451, 411, 413; 426/423

[56] References Cited

U.S. PATENT DOCUMENTS

| | | | |
|---|---|---|---|
| 3,519,538 | 9/1968 | Messing et al. | 435/176 |
| 3,556,945 | 1/1971 | Messing | 435/176 |
| 3,639,558 | 2/1972 | Csizmas et al. | 435/177 X |
| 3,669,841 | 6/1972 | Miller | 435/176 |
| 3,830,699 | 8/1974 | Zaborsky | 435/181 |
| 4,229,534 | 10/1980 | Defilippi | 435/180 X |
| 4,243,692 | 1/1981 | Scholze et al. | 435/176 X |

*Primary Examiner*—David M. Naff
*Attorney, Agent, or Firm*—Robbins & Laramie

[57] ABSTRACT

An improved immobilized enzyme composite is prepared by subjecting a siliceous carrier to an initial treatment with alkali, then acid, then reacting the carrier with an organosilane. The organosilane may then be coupled through a covalent coupling agent with an enzyme. The alkali-acid treatment provides an exceptionally high number of hydroxyl groups per unit volume, so that the treated carrier is especially useful in the preparation of high performance immobilized enzyme compositions, particularly by multi-layering immobilization, providing a very high amount of enzyme activity per unit volume. Multi-layering is accomplished by successive steps of bonding a difunctional covalent coupling agent to a previously immobilized enzyme layer, then bonding an additional layer of enzyme to the coupling agent. This may be repeated to apply as many layers as desired.

22 Claims, 4 Drawing Figures

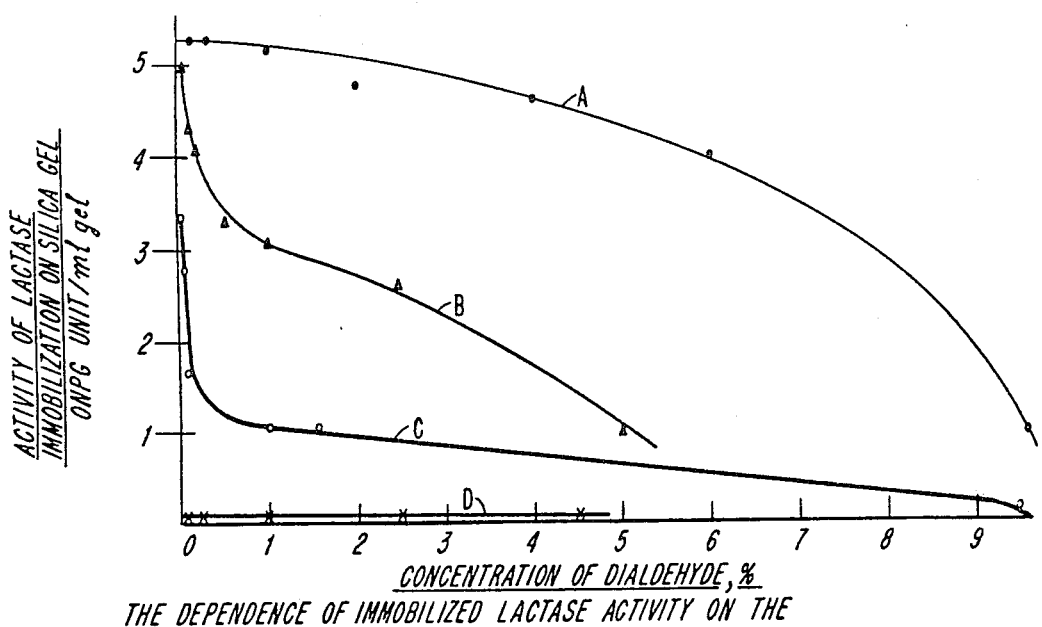

THE DEPENDENCE OF IMMOBILIZED LACTASE ACTIVITY ON THE
CONCENTRATION OF DIALDEHYDE SOLUTIONS.
  A. – ETHANEDIAL
  B – GLUTARALDEHYDE
  C – O-PHTHALDIALDEHYDE
  D – P-PHTHALDIALDEHYDE
THE SUPPORT MATRIX IS SILICA GEL.

Fig.1

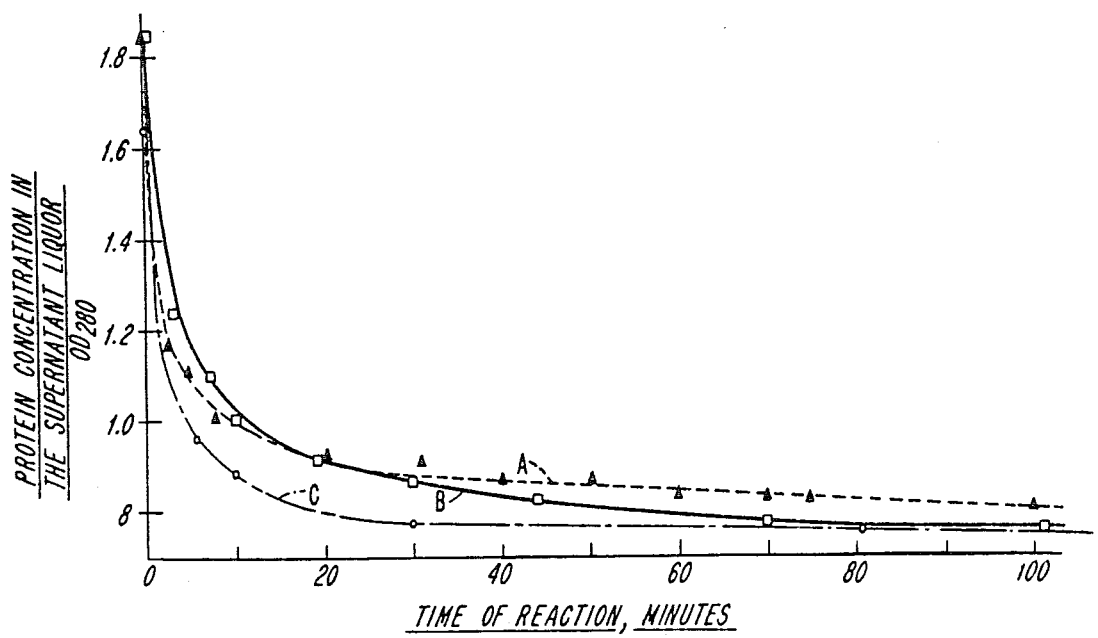

ENZYME COUPLING KINETICS WITH DIALDEHYDES AS IMMOBILIZING
REAGENTS AT ROOM TEMPERATURE.
  A – ONE LAYER IMMOBILIZATION WITH GLUTARALDEHYDE
  B & C – ONE LAYER AND TWO LAYER IMMOBILIZATION WITH ETHANEDIAL

Fig.2

THE TEMPERATURE DEPENDENCE OF THE IMMOBILIZED LACTASE ACTIVITY ON ONPG.
THE IMMOBILIZING REAGENT IS ETHANEDIAL AND THE SUPPORT MATRIX IS SILICA GEL.

THE TEMPERATURE STABILITY OF IMMOBILIZED LACTASE ACTIVITY ON ONPG.
THE IMMOBILIZING REAGENT IS ETHANEDIAL AND THE SUPPORT MATRIX IS SILICA GEL.

ACTIVATION OF A SILICEOUS CARRIER FOR ENZYME IMMOBILIZATION

This application is closely related to a copending patent application of ours, Ser. No. 148,012, filed May 8, 1980, which application is incorporated herein by reference.

INTRODUCTION

This invention relates to an improved process for activating a siliceous carrier to which a biologically active material, especially an enzyme, can be covalently coupled. More particularly, the invention relates to the preparation of a siliceous carrier for use in preparation of a multi-layered immobilized enzyme composite characterized by high activity per unit volume.

BACKGROUND

Enzymes are proteinaceous catalytic materials that have great industrial potential. Enzymes also are often very expensive materials. They are generally soluble in their respective substrates and except where the conversion product is of great value, recovery of the enzyme for reuse may be difficult or impossible. In some cases, the processing conditions may destroy the enzyme. Where the enzyme is not destroyed, it may be necessary to destroy it, as in some food products, where continued activity would have an unwanted effect.

To avoid these problems, fixed or immobilized enzyme systems have been developed in recent years. Procedures such as adsorption, encapsulation, and covalent bonding are routinely used with many enzymes. The immobilization procedure selected, from the many available, produces a composition that can be used in either batch or continuous processes, but that is most advantageously used in a continuous process for economy.

While the term "insolubilized enzyme" has been used in the past on occasion, as in U.S. Pat. No. 3,519,538, to refer to an enzyme coupled by covalent chemical bonds to an insoluble inorganic carrier, and thus rendered not soluble in water, the term "immobilized" is used herein to refer to such an enzyme, or other biologically active material, fixed to a carrier.

The term "stabilized" is used herein to refer to a biologically active material, such as an enzyme, that has been stabilized against the loss of activity that would otherwise occur because of aging or exposure to an elevated temperature, or use in a reaction as a catalyst.

In the process of immobilizing an enzyme, there are many important practical considerations. There should be as little loss of enzyme activity as possible. The cost of immobilization should be low. The carrier material should be one that does not have a deleterious effect on the action of the enzyme during the process in which it is to be used. The immobilized enzyme should not leak enzyme or any other material into the reaction mixture, especially in food processing applications. The activity of the enzyme should remain high over a long period of operating (reaction) time, generally measured, in industrial processes, as the half-life. In addition, the immobilized enzyme should offer good hydraulic characteristics, to permit reasonable throughput rates. Equally importantly, the immobilized enzyme should be able to withstand reasonable operating temperatures, to permit practical operating rates, with the least feasible loss of activity.

For economy, it is also desirable that recharging of the carrier be possible, to reactivate spent immobilized enzyme, preferably by as simple an operation as possible.

Work in the field has progressed from concern simply with trying to immobilize an enzyme on a water-insoluble carrier to more sophisticated work in which the objective was to produce an immobilized enzyme that would deal successfully with all of the practical considerations mentioned above.

Several United States patents describe advances in the art that are representative of what has been done.

In U.S. Pat. No. 3,519,538, Messing and Weetall describe an immobilized enzyme composition in which the enzyme is covalently coupled to an inorganic carrier through an intermediate silane coupling agent, the silicon portion of the coupling agent being attached to the carrier and the organic portion of the coupling agent being attached to the enzyme. While glass of controlled porosity was the preferred carrier material, a wide variety of inorganic carrier materials, often siliceous, are disclosed as being useful. The carrier was prepared for use by substantial exposure to nitric acid, followed by furnacing in an oxygen atmosphere.

In almost all of the instances in which a particulate, siliceous carrier material is employed for initial reaction with a organosilane, the carrier particles are intially activated so as to present, at their surfaces, either oxygen or hydroxyl groups or both. The hydroxyl groups ordinarily are produced by reaction of the siliceous particles with a strong acid. Thus, Messing and Weetall in U.S. Pat. No. 3,519,538 washed powdered porous silica glass in 0.2 N nitric acid at 80° C. with continuous sonication for at least three hours. The glass was then washed several times with distilled water, and then heated to 625° C. overnight in the presence of oxygen. The treated glass was then considered to be ready for reaction with gamma-aminopropyltriethyoxysilane. Trypsin was coupled to the silated glass through the use of a covalent coupling agent.

In U.S. Pat. No. 3,556,945, Messing used an enzyme having available amine groups, and it was coupled to a porous glass carrier through reactive silanol groups, by means of amine-silicate bonds and by hydrogen bonding. Once again, the carrier was prepared for use by an acid treatment, coupled with heating in a furnace.

In U.S. Pat. No. 3,669,841, Miller describes immobilized enzyme compositions in which the enzyme is attached to siliceous materials by silation of the carrier, and linking to an enzyme by a crosslinking agent. No pretreatment of the carrier particles is mentioned. In Example 1 of the patent, gamma-aminopropyltrimethoxysilane is reacted with particulate silica, then an enzyme is added with stirring, and then an aqueous formaldehyde solution is added. In Example 3, a calcium silicate carrier, in a form not specified, was "dry coupled with 0.25 weight percent gamma-aminopropyltrimethoxysilane, was slurried in water (50 ml.) and *B. subtilis* enzyme mixture" was added to the slurry. The pH of the slurry was adjusted to 8.0 and glutaraldehyde was added as a covalent coupling agent. At the point in the example where the pH was alkaline, the calcium silicate carrier had already been reacted with the organosilane.

BRIEF SUMMARY OF THE PRESENT INVENTION

According to the present invention, particulate siliceous carrier materials are prepared for reaction with an organo-silane, as an initial step in the preparation of an immobilized enzyme or similar composite, by reaction with an alkali, followed by an acid treatment, to generate a large number of reactive -OH groups on the carrier material surface per unit volume. The degree of hydrolysis that is involved depends on pH, temperature, and reaction time.

In a preferred embodiment of the invention, a commercial silica gel, having a particle size in the range from about 35 mesh to about 230 mesh, U.S. Standard Sieve size, is reacted with a strong base, then with a strong acid, to generate free hydroxyl groups at the surface of the carrier particles. The activated siliceous carrier particles are then reacted with the organosilane, to provide a silated base to which an enzyme or other biologically active material, having available amine groups, can be coupled using a difunctional coupling agent such as a dialdehyde. The biologically active material is preferably an enzyme, and most preferably is lactase (EC 3.2.1.23), but may be an antigen, an antibody, a hormone, or other proteinaceous material, provided the biologically active material has an available reactive group for coupling, preferably an amine group.

Generally, hydrolyzable silane having amine substituent is coupled to the hydroxyl groups on the activated carrier particles. A polyfunctional coupling agent is then reacted with the amine groups of the silane. Preferably, the polyfunctional material is a polyaldehyde or a bis-imidate, but other such materials may be used. Next, after removal of unreacted material, the biologically active material, such as an enzyme, having available amine groups, is reacted with the free (unreacted) aldehyde groups. This step covalently bonds the enzyme or other material to the carrier, without substantial loss of activity.

At this stage, there is a single amount or "layer" of material, such as enzyme, immobilized by covalent bonding to the carrier. The activity available per unit volume should be higher than has been possible heretofore, because of the high concentration of reactive hydroxyl groups available on the siliceous carrier per unit volume.

The immobilized material, preferably enzyme, has available amine groups, and these are reacted in turn with an additional amount of a polyaldehyde, preferably glyoxal. After washing, additional material, such as enzyme, is added, and covalently bonds through its available amine groups with the unreacted aldehyde groups, to form a covalent bond between the added material and the initially immobilized material.

When all of the immobilized material is enzyme, there are two immobilized enzyme "layers", one covalently bonded to the carrier, and the other covalently bonded to the initially immobilized "layer" of enzyme. The word "layer" is not aptly descriptive; the term is used for convenience and because those skilled in the art will understand it.

The process may be repeated as often as desired, to form a multi-layered immobilized composition. This composition can be prepared so as to retain high activity, has high activity per unit volume, and can be prepared to have unusually good thermal stability, good half-life, and practical mechanical strength.

In a preferred embodiment, the carrier material is a finely divided, free-flowing particulate siliceous material, most preferably a silica gel, and the immobilized material is the enzyme, lactase (EC 3.2.1.23). Such immobilized lactase may be used to convert whey into more useful products.

BRIEF DESCRIPTION OF THE DRAWINGS

In the drawings:

FIG. 1 is a graph plotting the units of activity per ml. of single layer immobilized enzyme composition prepared in accordance with certain embodiments of the invention, where lactase is immobilized on silica gel through the use of each of four different dialdehyde cross-linking reagents, employed at different concentrations for comparative purposes, showing the concentration dependence of the dialdehydes;

FIG. 2 is a graph plotting protein (enzyme) concentration against reaction time in minutes, showing the progress of immobilization and the decrease in enzyme concentration for first layer immobilization of lactase with glutaraldehyde, Curve A, and for first layer and second layer immobilization with glyoxal, Curves B and C respectively;

DETAILED DESCRIPTION OF THE INVENTION

Figure 3:
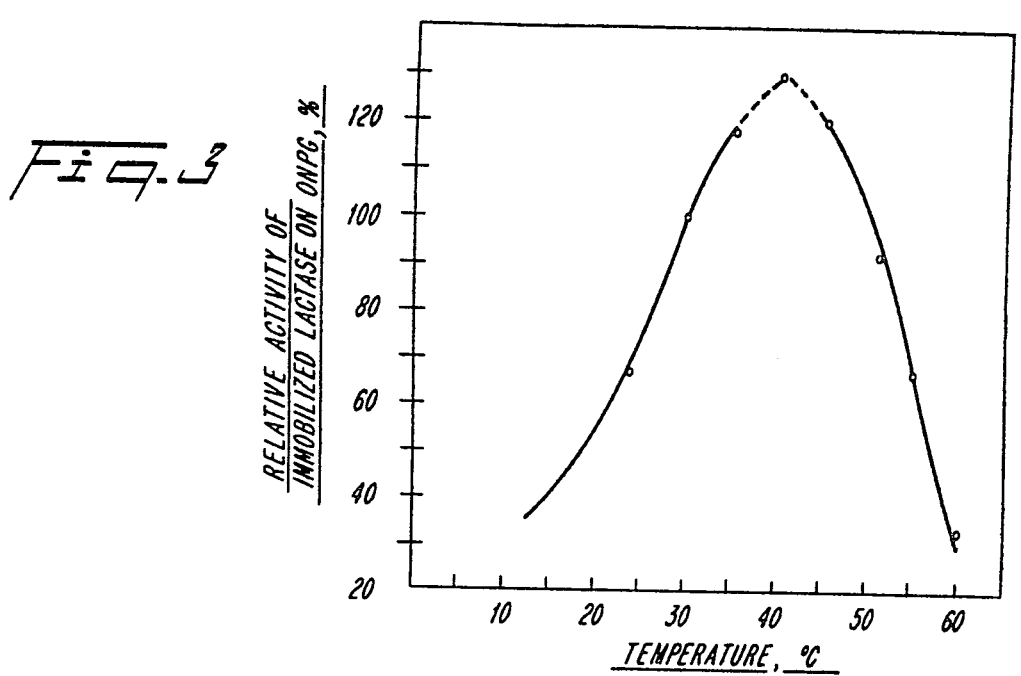
FIG. 3 is a plot of the activity of immobilized lactase on ortho-nitrophenyl galactopyranoside (ONPG) as a substrate, at different temperature.

To make an immobilized enzyme composition in accordance with the present invention, the carrier material is preferably in particulate form, most preferably finely divided and free-flowing, but in addition, may be in the form of fibers, tubes, sheets, beads, or porous glass. In any form, it should provide a very high surface area per unit volume.

The carrier may be any chemically inert natural or synthetic siliceous material. Such material includes granulated, fibrous and finely particulate silica. The carrier material may also be, for example, porous glass, or any such siliceous material that has or can be formed to have a shape that makes processing practical in the desired end use, that offers a high surface area per unit volume, and that either has or can be treated to have active hydroxyl groups at its surface that can react with hydrolyzable groups of an organosilane or cyanogen bromide coupling agent.

In a preferred embodiment, a silica gel is treated with a strong base, then with a strong acid, in order to activate it by generating hydroxyl groups at the surface of the gel particles. The hydrolysis of the Si-O-Si groups at the surfaces of particles of silica gel is pH-dependent. The rate and extent of hydrolysis rises as the temperature rises at a given pH, and also rises as the pH rises. The preferred conditions for the practise of the present invention involve the use of a 0.5 M solution of NaOH (about 2% concentration by weight) or of KOH. Both of these have a pH > 13.

It is possible to produce at least five times as many -SiOH groups (in the form of SiONa, SiOK, or the like) on silica gel at pH > 11 than at neutral or acid pH, at 20° C. Stated another way, more than five times as much hydrolysis occurs per unit volume at pH>11 than at a neutral or acid pH.

Since under strongly basic conditions, i.e., pH>11, the silanol groups exist as $-SiO^-Na^+$, or $-SiO^-K^+$, or the like, it is necessary to remove the metal ions by neutralizing with a strong acid, such as nitric acid, to restore the hydroxyl groups to make them available for further chemical reactions.

One objective of the invention is to produce the greatest feasible number of available, reactive SiOH groups per unit volume, without serious impairment of carrier integrity. Optimization requires careful attention to the three key parameters of pH, temperature, and reaction time.

The strong base is preferably an aqueous solution of sodium hydroxide or potassium hydroxide, preferably employed at a concentration of from about 0.1% to about 5%, preferably 1% to 5% at 20° C.–45° C., for thirty minutes to two hours or more. Other highly basic materials may also be used, such as, for example, mixtures of alkali metal and alkaline earth metal hydroxides; sodium carbonate and potassium carbonate (pH>12); ammonium hydroxide; and mixtures of two or more of these. Calcium hydroxide (pH about 10.5) is not a good choice, because of possible problems related to precipitation of poorly soluble or insoluble materials. However, theoretically at least, any aqueous reactant at a pH>10 can be employed to initiate activation of the silica gel. The particular reaction temperature, time of reaction, and strength of the alkaline reactants selected will be dependent upon the stability of the siliceous carrier being used.

The acid used to remove metal ion from the carrier, to generate reactive hydroxyl groups, is preferably a strong acid that forms a soluble salt with the metal ion, for ease in rinsing. Any of the mineral acids may be used, as may several of the other organic and inorganic acids. The mineral acids are preferred for efficiency, economy, and ready availability.

The activated carrier is reacted with a coupling agent, preferably a silane that couples to the hydroxyl groups of the carrier at one portion of the silane molecule, and that provides at a remote part of the silane molecule a reactive amine group.

The preferred kind of silane coupling agent has the formula:

$$H_2N-R-Si(OR_1)_3$$

where R is an alkylene group, and $R_1$, of which there are three per molecule, is preferably alkyl, most preferably lower alkyl. The three $R_1$ substituents may be the same or different on a given molecule.

In the next step, a suitable amount of a polyfunctional reactant, preferably a polyaldehyde, and most preferably glyoxal (ethanedial), in a suitable solvent medium, is brought into contact with the amine-reactive silica gel or other carrier. In preferred embodiments, this makes the silica gel aldehyde-reactive or aldehyde-functional.

The aldehyde-functional carrier is then mixed with enzyme (or other biologically active material) having available amine groups. The available amine groups of the enzyme react with the free aldehyde groups of the carrier, to immobilize the enzyme on the carrier. The composite is then washed to remove excess unreacted materials.

The immobilized enzyme now consists of a carrier to which a first amount or layer of enzyme is covalently bonded. The enzyme is one having available amine groups.

As pointed out above, the alkali treatment should result in the production of at least five times as many hydroxyl sites as any acid treatment. While in practise this may occur, in the enzyme immobilization step, theoretical and practical difficulties prevent the realization of 100% of this increase in terms of increased enzyme immobilization, but nevertheless, a definite gain ensues. In Table 1 below, a comparison is made of immobilized lactase, first when the silica gel carrier has been activated by an acid treatment, then when the silica gel carrier has been activated by an alkali-acid treatment as described above. Except for the activating reagents used, the immobilization techniques were essentially the same. In trial comparisons 3 and 6, both the acid and the alkali-acid activating treatments were used, for comparative purposes. As the data in Table 1 demonstrates, the alkali-acid treatment of the present invention always resulted in higher activity per unit volume.

TABLE 1

IMMOBILIZATION OF LACTASE IS INCREASED BY TREATING SILICA GEL WITH STRONG ALKALI, THEN ACID

| Covalent Bonding Reagent | Immobilized lactase activity at 30° C. (single layer), units of enzyme/units of gel volume | |
|---|---|---|
| | HNO₃ activation | NaOH-acid activation |
| Ethanedial | | |
| trial 1 | 3.43 | — |
| trial 2 | 4.47 | — |
| trial 3 | 4.32 | 5.50 |
| trial 4 | — | 7.29 |
| trial 5 | — | 6.03 |
| Glutaraldehyde | | |
| trial 6 | 3.19 | 4.93 |
| trial 7 | — | 5.23 |
| trial 8 | — | 5.18 |

Note:
1. ONPG (ortho-nitrophenyl galactopyranoside) was used as lactase substrate.
2. The immobilized lactase activity was determined at its optimum pH.

In the next step of making a multilayered immobilized emzyme composite, the single layer immobilized enzyme composition is reacted with a polyfunctional material, most preferably glyoxal, so that it becomes aldehyde-functional. It is then reacted with a second amount of enzyme, which in turn becomes covalently bonded, this time through the glyoxal to the initially immobilized layer of enzyme. This process can then be repeated to add as much as enzyme as desired to the composition. Generally not more than 10 layers are practical, and most preferably a total of four layers are applied when the enzyme is lactase and the carrier is silica gel. When proper procedures are employed with careful control over the amounts of reactants and with the removal of excess reactants, there is relatively little observed loss of enzyme activity.

The reaction of aldehyde and amine groups takes place readily even at low temperatures, so that the reaction can be conducted at 5° C. in solution, and from slight acidity to a moderate pH range. The pK values of the alpha-amino groups in most enzymes and other polypeptides fall in the range from about 7 to about 8. Thus, most enzymes and other such polypeptide materials may be immobilized at a pH that is very close to being neutral, which is a mild condition that sustains activity.

In practicing the present invention, it is important to avoid unwanted cross-linking that may occur. The extent of cross-linking can be limited by careful control over the amount and concentration of cross-linking agent, such as glyoxal, that is employed, and by washing to remove unreacted excess cross-linker as soon as the covalent bonding has had a reasonable opportunity to go to completion.

With proper limitation of the cross-linker and of its reaction, when lactase is immobilized according to the invention in multiple layers on silica gel, using glyoxal as the polyfunctional agent, the amount of enzyme activity retained corresponds to the activity described by the ratio, for a three layer structure, of 100% to 70%-95% to 70%-95%. This ratio relationship is employed as a descriptor of cumulative activity, but at this time it is not known in which layer (if in any single layer) the decrease occurs. Limited cross-linking stabilizes the immobilized enzyme; too much reduces the activity. Some cross-linking, with consequent reduction in activity, seemingly cannot be avoided.

The increase in the amount of enzyme activity per unit volume in the initial immobilized layer, achieved by the present invention, is very important because of the multiplier effect that is observed as additional layers are applied. That is, the "density" of immobilized enzyme is important because each initial immobilized molecule provides a reaction site to which more enzyme can be immobilized, so that the "density" of the initial immobilized layer can control the "density" of all subsequent layers.

Immobilized multilayered lactase on a silica gel carrier, prepared in accordance with the invention, is generally characterized by advantageously high activity per unit volume; high mechanical and thermal stability; and prolonged half-life.

The invention will now be further illustrated by several specific demonstrations of the practice of preferred embodiments thereof. In this application, all parts and percentages are by weight, and all temperatures in degrees Celsius, unless expressly stated to be otherwise.

EXAMPLE 1

Preparation of Chemically Active Groups on Surface of Support Matrix—Silica Gel

Step A. Preparation of Propylamine Silica Gel 10 g. of silica gel, $(SiO_2)_n$, 35–70 mesh, ASTM, from E. Merck, Darmstadt, Germany, was activated by suspending it in 50 ml of 2% NaOH solution. The mixture was heated and maintained at 40° C. for 1½ hours with occasional gentle stirring. The alkaline solution was then filtered off on a plastic frit-funnel, and the residual gel was then suspended in 50 ml of 20% $HNO_3$ solution to neutralize residual alkali and remove metal ion from the gel.

The resulting hydrophilic silica gel was then added to 50 ml of 4% gamma-aminopropyl triethoxy silane solution which had been adjusted to pH 5.0 with acetic acid. The gel-silane reagent mixture was heated and maintained at 65°–75° C. for 1½ hours with stirring. The silane solution was then decanted.

The propylamine silica gel product was neutralized with 4% KOH solution to about pH 7.5, then washed exhaustively with distilled water on a plastic frit-funnel, and then vacuum dried for storage. It could be used as is, without drying. This propylamine silica gel product can be used as a carrier for immobilization thereto by covalent bonding, as with a dialdehyde such as glyoxal, of any biologically active compound that has an available amine group, such as enzymes, hormones, immunoreactants, and the like. The general technique is particularly useful for the preparation of an enzyme electrode.

Step B. Preparation of Aldehyde Silica Gel 25 ml of the propylamine silica gel of Step A was mixed in a flask with 50 ml of 0.1% ethanedial (glyoxal) solution in 0.1 M potassium phosphate buffer, pH 8.0, which contained 1% reagent alcohol. The flask was immediately evacuated and filled with $N_2$ gas, then heated to about 40° C. for 1½ hours with occasional gentle shaking. The aldehyde silica gel was then filtered on a plastic frit-funnel, washed with distilled $H_2O$, and immediately vacuum dried for storage. The container was filled with $N_2$ gas to prevent oxidation.

Step C. Preparation of Immobilized Lactase Enzyme on Silica Gel 25 ml of the aldehyde silica gel was added to 50 ml of diluted Lactozym 750L lactase (NOVO Industri AS, Denmark) in 0.1 M potassium phosphate—5 mM $MgSO_4$—pH 7.3, the amount of enzyme being in excess of the amount required for coupling. The reaction vessel was immediately evacuated. The reaction proceeded at room temperature for 1 hour with occasional gentle shaking.

The lactase-silica gel product was filtered on a plastic frit-funnel to remove the excess enzyme, and washed with washing buffer (0.02 M potassium phosphate, 5 mM $MgSO_4$, pH 7.0). The lactase-silica gel was then suspended in enzyme buffer (0.04 M potassium phosphate, 5 mM $MgSO_4$, pH 7.0) and stored at 4° C.

Step D. Multiple Layer Immobilization of Enzyme 25 ml of lactase silica gel (sedimented gel volume) was added to 50 ml of 0.1% ethanedial solution in enzyme buffer (0.1 M potassium phosphate, 5 mM $MgSO_4$, pH 7.3) which contained 1% reagent alcohol, and the flask was then evacuated. The mixture was reacted at room temperature for 1½ hours with occasional mild shaking.

The aldehyde-functional enzyme gel was filtered and washed with washing buffer at pH 7.0, then immediately added to 50 ml of diluted Lactozym 750L lactase (20× dilution by volume, NOVO Industri AS, Denmark) solution, again in enzyme buffer (0.1 M potassium phosphate, 5 mM $MgSO_4$, pH 7.3). This mixture was reacted about 1 hour at room temperature.

The silica gel carrier, now having two "layers" or applications of lactase immobilized thereon, was filtered and washed with washing buffer at pH 7.0, suspended in enzyme buffer at pH 7.0, and stored at 4° C.

Third, fourth and even more "layers" of enzyme have been immobilized by repeating this same procedure, with relatively little loss in activity.

Step E. Regeneration of Enzyme Silica Gel Activity

After use, spent lactase silica gel, whether from single layer or multiple layer immobilization, which may retain some relatively low level of lactase activity can be regenerated to increase and restore its lactase activity by following a similar procedure to that described in Step D. The spent enzyme gel still contains covalently linked proteinaceous material, having available amine groups, which can be reacted with ethanedial, followed by lactase immobilization as in Step D.

EXAMPLE 2

Multiple Enzyme Immobilization

A procedure similar to that in Step D of Example 1 was followed, except that, for the layers of enzyme applied subsequent to the first, lipase (Marshall lipase, Miles Laboratories, Inc.) was used instead of Lactozym 750L.

This immobilized enzyme composition exhibits the enzyme activites of both lactase and lipase. It is therefore useful for the production of lipolyzed cream and butter oil. The controlled-lipolysis of such products can enhance the buttery flavor and/or can be used in a variety of products.

Similarly, the procedure of Step D of Example 1 was followed, except that the enzyme applied, for layers subsequent to the first, was the protease bromelin (Midwest Biochemical Corp. U.S.A.). This immobilized enzyme composition exhibited the enzyme activities of both lactase and protease. It was useful for the hydrolysis of the sugars and proteins in cheese whey.

In similar fashion, following a procedure similar to that in Step D of Example 1, the enzyme employed for application subsequent to the first layer may be a mixture of lipase and protease. The resulting immobilized enzyme composition will exhibit the activity of all three enzymes, that is, of lactase, lipase, and protease. Such a composition is useful in the processing of dairy products for the controlled hydrolysis of lactose, and whey proteins, as well as the controlled lipolysis of lipids for enhanced flavors.

Alternatively, spent immobilized enzyme may be employed as the base on which to immobilize enzymes other than the original enzymes, following generally the procedure of Step E of Example 1.

EXAMPLE 3

Evaluation and Comparison of Different Dialdehydes in Immobilization

The procedure of Example 1 was followed to immobilize lactase on silica gel, with the use of glyoxal as the coupling agent, and for comparative purposes, with the use of other dialdehydes in place of glyoxal.

Four structurally preferred, different dialdehydes were tested for suitability for immobilizing. Their chemical formulae are as follows:

| | |
|---|---|
| ethanedial (glyoxal) | OHC—CHO |
| n-pentanedial (glutaraldehyde) | OHC—CH$_2$—CH$_2$—CH$_2$CHO |
| o-phthaldialdehyde | 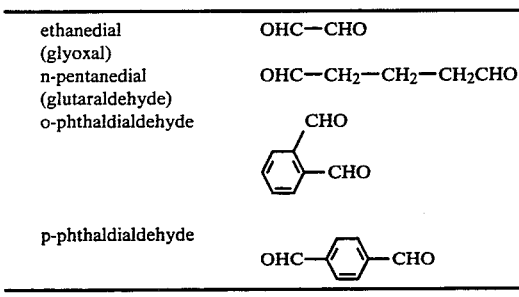 |
| p-phthaldialdehyde | |

The concentration dependence of the dialdehydes as immobilizing reagents is shown in FIG. 1. The ethanedial appears to be the best one, with highest enzyme activity retention (concentration of ethanedial from about 0.03% to about 1%). The glutaraldehyde and O-phthaldialdehyde are less effective and only comparably effective in a very narrow low concentration range (<0.3%). p-phthaldialdehyde appears to exhibit a very low level of usefulness.

The amount of enzyme and the immobilization reaction kinetics for lactase immobilized on aldehyde silica gel with ethanedial and with glutaraldehyde respectively are somewhat similar. The immobilization time course and the disappearance of enzyme concentration in the supernatant liquid for first layer and second layer immobilization of lactase are shown in FIG. 2.

Figure 4:
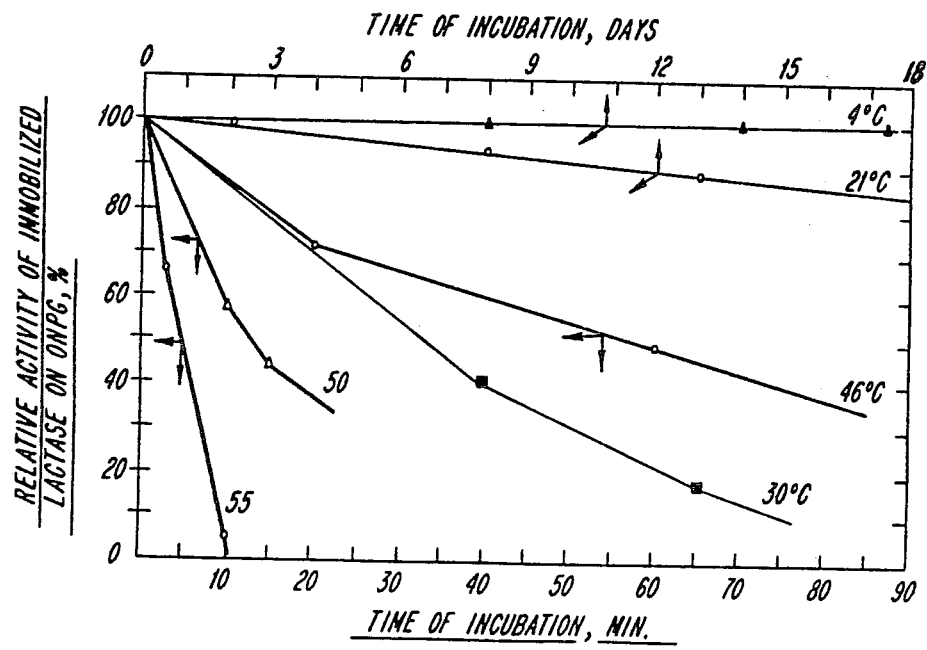
FIG. 4 is a plot of the activity of immobilized lactase against time of incubation with ONPG as a substrate, at different temperatures, the arrows on the several curves indicating the applicable time scale, i.e., whether the time was measured in minutes or days.

The temperature dependence and the temperature stability of the immobilized lactase activity are shown in FIGS. 3 and 4 respectively. The comparison of thermal stability of lactase immobilized with ethanedial and with glutaraldehyde is shown in Tables 1 and 2. The enzyme activity and its active conformational stability can be effectively increased by multi-layer immobilization technique, as shown in Tables 2, 3 and 4.

Again, the relative thermal stability and immobilized lactase activity by layered-immobilization are both significantly improved, and appear to be much better with ethanedial than with glutaraldehyde. Generally speaking, glutaraldehyde is a good immobilizing reagent, but ethanedial is preferred.

The immobilized enzyme composition of Ex. 1 is useful in treating whey solutions to improve their sweetness. When the immobilized enzyme is a combination of lactase and glucose isomerase, a very sweet product is produced.

Definitions

Enzyme Activity Unit and Analytical Method.

Lactase activity—1 ONPG unit is defined for free enzyme as the hydrolysis of 1 umole of ONPG per minute at 30° C. in buffer (0.02 potassium phosphate, $10^{-4}$ M M$_n$Cl$_2$, pH 7.0); and for immobilized enzyme, in 0.066 mole potassium phosphate at pH 6.75.

ONPG—ortho-nitrophenyl galactopyranoside

Lactose determination—use Shaffer-Somogyi micromethod, A.O.A.C., 31.052.

Glucose determination—use Worthington Statzyme Glucose (500 nm).

TABLE 2

Comparison of the temperature stability of immobilized lactase activity with different dialdehydes as immobilizing reagents, respectively. The support matrix is silica gel. Incubation temperature is 50° C.

| | Immobilized lactase activity after incubation at 50° C. | | | | | |
|---|---|---|---|---|---|---|
| | Mono-layer | | | Double Layer | | |
| Immobilizing Reagent | 0 min. | 10 min. | 15 min. | 0 min. | 10 min. | 15 min. |
| Ethanedial | 100% | 30.8% | 17.9% | 100% | 47.9% | 24.0% |
| n-Pentanedial | 100% | 20.6% | 12.6% | 100% | 29.3% | 5.9% |
| o-Phthaldialdehyde | 100% | 0% | 0% | 100% | 0% | 0% |

NOTE:
1. ONPG was used as lactase substrate.
2. The immobilized lactase activity was determined at its optimum pH.

TABLE 3

Immobilized lactase activity is increased by layering of the enzyme with alkyl dialdehyde, with ethanedial giving the best conformational stability.

| Immobilizing Reagent | Immobilized lactase activity at 30° C., unit/enzyme gel volume | | | | | |
|---|---|---|---|---|---|---|
| | One Layer | | Two Layers | | Three Layers | |
| | ONPG/ml | Percentage | ONPG/ml | % Increase | ONPG/ml | % Increase |
| Ethanedial | | | | | | |
| Run 1 | 4.32 | 100% | 7.68 | 77.8% | — | — |
| Run 2 | 4.32 | 100% | 7.52 | 74.1% | 10.76 | 149.1% |
| Run 3 | 4.32 | 100% | — | — | 10.23 | 138.9% |
| Run 4 | 7.29 | 100% | 12.74 | 75% | 14.86 | 170.2% |
| Run 5 | 5.50 | 100% | 9.60 | 94.7% | — | — |
| Glutaraldehyde | | | | | | |
| Run 1 | 3.19 | 100% | — | — | 9.44 | 195.9% |
| Run 2 | 4.93 | 100% | — | — | 10.1 | 104.9% |

Note:
1. ONPG was used as lactase substrate.
2. The immobilized lactase activity was determined at its optimum pH.

TABLE 4

Immobilized lactase enzyme activity is stabilized by enzyme layers which are fixed with ethanedial. Support matrix is silica gel.

| Enzyme Layers | Immobilized lactase activity after incubated at 50° C. | | |
|---|---|---|---|
| | 0 min. | 10 min. | 15 min. |
| 3 layers | 100% | 53.3% | 40.6% |
| 2 layers | 100% | 47.9% | 24.0% |
| 1 layer | 100% | 30.8% | 17.9% |

Note:
1. ONPG was used as lactase substrate.
2. The immobilized lactase activity was determined at its optimum pH.

TABLE 5

Average half-life of immobilized lactase at 50° C. under assay buffer conditions. Lactase was immobilized on silica gel with ethanedial as immobilizing reagent.

| Layers of lactase | Half-life at 50° C. |
|---|---|
| 3 layers | 11.5 min. |
| 2 layers | 8.5 min. |
| 1 layer | 5.5 min. |

NOTE:
1. Immobilized lactase activity was determined at its optimum pH.
2. ONPG was used as lactase substrate.

GENERAL

To practice the invention, the siliceous material can be alkali treated, the metal ion removed, then the hydrophilic siliceous material can be reacted with the organosilane in any convenient manner, by contacting the former with the latter to obtain the desired bonding through hydrolyzable groups of the organosilane.

The treatment of the siliceous carrier with a base involves bringing a solution of a strong base, such as sodium hydroxide or potassium hydroxide or a mixture thereof, or the equivalent, into contact with the carrier over a sufficient period of time and at an appropriate temperature to generate -OM groups, where M is a metal, then removing the metal ion with acid to generate residual hydroxyl groups, for optimum reaction with the organosilane. If the surfaces of the carrier material are not already clean, sonication or the like may be employed, simultaneously with the alkali treatment, for cleaning purposes.

Generally, the solution of strong base, if an alkali metal hydroxide, is employed at a concentration in the range of from about 0.1%, or preferably, about 1%, to about 5%, and at room temperature (20° C.) or at a slightly elevated temperature. A preferred temperature range is from about 25° C. to about 45° C., although higher temperatures may be employed if desired. When the base is an aqeous solution of sodium hydroxide, for example, at a concentration in the range from 1% to 5%, and at a temperature in the range from about 25° C. to about 45° C., the siliceous carrier should be treated with the base solution for a period of time in the range from about 30 minutes to about 2 hours.

Care must be taken in treating the siliceous carrier material, so that it remains in solid form and does not go into solution to such an extent as to make the treatment inefficient. To avoid dissolution of the carrier, silica gel, porous glass particles, porous glass disks and the like, are preferred to other siliceous carrier materials which may have a tendency to go into solution during any prolonged treatment with a strong alkali. For the more readily soluble siliceous carrier materials, the base employed may be sodium carbonate, potassium carbonate, mixtures of these with their hydroxides, highly basic sodium phosphates, ammonium hydroxide (pH about 10), and the like.

For the purposes of the present invention, ammonium hydroxide can be considered to be the equivalent of an alkali metal hydroxide, and the ammonium ion can be considered to be an alkali metal ion.

A strongly acidic material, generally a mineral acid, is used to remove metal ion. It should be one that forms readily soluble salts that go into solution and rinse off the carrier easily, leaving hydroxyl groups on the carrier surfaces in large numbers.

Usually the organosilane is dissolved in an inert solvent such as toluene, xylene, or the like, and the resulting solution is then applied to the siliceous material. Aqueous solutions of a soluble silane can also be used.

The amount of organosilane coupling agent employed is dependent upon the nature and surface area of the siliceous material. Usually, at least about 0.01 percent by weight of the organosilane, based on the weight of the siliceous material, is used. Amounts in the range from about 0.25% to about 2% by weight are preferred.

Suitable organosilanes include substituted organosilanes which can be represented by the formula

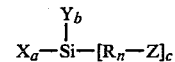

where X is a hydrolyzable group capable of reacting with a hydroxyl group, Y is hydrogen or monovalent hydrocarbon group, R is an alkylene group having from 1 to about 20 carbon atoms, Z is a functional group capable of reacting with a crosslinking agent, n is an integer haing a value of 0 or 1, a is an integer having a value of 1 to 3, inclusive, b is an integer having a value 0 to 2, inclusive, c is an integer having a value of 1 to 3, inclusive, and the sum of a+b+c equals 4.

Examples of suitable X groups include halo, hydroxy, alkoxy, cycloalkoxy, aryloxy, alkoxy-substituted alkoxy such as beta-methoxyethoxy or the like, alkoxycarbonyl, aryloxycarbonyl, alkyl carboxylate, and aryl carboxylate groups, preferably having eight or less carbon atoms.

Examples of suitable Y groups in the above formula are hydrogen, methyl, ethyl, vinyl, isobutyl, and other hydrocarbyl groups, preferably having 10 or less carbon atoms.

The R group in the above formula can be any alkylene group having up to about 20 carbon atoms, and preferably from about 2 to about 18 carbon atoms. Examples of such groups are ethylene, the propylenes, the butylenes, the decylenes, the undecylenes, the octadecylanes, and the like.

The Z groups can be any functional group capable of reacting with the hereinbelow defined crosslinking agent. Examples of such groups are amino, primary and secondary amido, epoxy, isocyanato, hydroxy, alkoxycarbonyl, aryloxycarbonyl, vinyl, allyl, halo such as chloro or bromo, and the like.

Particularly preferred of such functional groups are amino.

Particularly preferred organosilanes for the purposes of this invention are omega-aminoalkyl and aminoaryltrialkoxysilanes such as gamma-aminopropyltrimethoxysilane, aminophenyltriethoxysilane, and the like.

For the purposes of this invention suitable crosslinking agents are dialdehydes, bis-imidoesters, bispropiolates and disulfonyl halides.

Illustrative dialdehydes are glyoxal, glutaraldehyde, malonic aldehyde, succindialdehyde, and the like, preferably containing from 2 to 8 carbon atoms, inclusive.

Illustrative bis-imidoesters are dimethyl adipimidate (DMA), dimethyl suberimidate (DMS), N,N'bis (2-carboximidoester) tartarimide dimethyl ester (CETD), dimethyl 3,3'-dithiobispropionimidate, and the like.

Illustrative bispropiolates are the diol propiolates such as ethylene glycol bispropiolate, propylene glycol bispropiolate, butylene glycol bispropiolate, hexamethylene glycol bispropiolate, decamethylene glycol bispropiolate, cyclohexylene glycol bispropiolate, methylolpropane diol bispropiolate and the like, as well as bisphenol A propiolate, pentaerythritol bispropiolate, and the like.

Illustrative disulfonyl halides are benzene-1,3-disulfonyl chloride, naphthalene-1,5-disulfonylchloride, naphthalene1,6-disulfonylchloride, naphthalene-2,5-sulfonylchloride, and the like.

The amount of crosslinking agent to be used is dependent principally on the amount of enzyme or enzymes that is desired to be incorporated into the composite. Usually an enzyme crosslinking agent molal ratio is about 1:1 or less. A ratio of about 0.01–0.0001/1.0 is preferred.

The bonding of the enzyme, the crosslinking agent and the organosilane, which is bonded to the alkali-treated siliceous material, can be carried out in any convenient inert medium, usually an aqueous medium at pH conditions and temperature which do not tend to inactivate the enzyme. Temperatures above about 60° C. should generally be avoided. The present process is readily carried out at ambient room temperature. The temperature of device depends, however, mainly on the particular enzyme or mixture of enzymes used. Usually the temperature can range from about −5° C. to about 30° C. A temperature in the range from about 0° C. to about 10° C. is preferred.

Generally the same conditions as mentioned above for immobilization of the initial enzyme layer apply to the immobilization of subsequent enzyme layers.

The dialdehydes are preferred polyfunctional agents for use in the present invention. As FIG. 1 and Table 2 indicate, the dialdehydes are equivalent in performance. Generally, those dialdehydes containing two through four carbon atoms are expected to perform equally well. Dialdehydes having three and four carbon atoms are not readily commercially available at the present time.

Glutaraldehyde (n-pentanedial) is not currently believed to be a simple five carbon molecule. Rather, it is believed to occur, in its commercially available form, as an oligomer, actually a trimer. This makes a substantial difference in the performance of this particular dialdehyde when used in the present invention, since the trimer form would be expected to and apparently does lend itself to the production of crosslinking between enzyme molecules within a given layer. Such intra-layer cross-linking is generally not regarded as desirable, since it apparently tends, based on available data, to reduce activity.

From FIG. 1, the conclusion can readily be drawn that the minimum amount of dialdehyde should be used that is sufficient to produce covalent bonding, and that when more than the minimum is employed, intra-layer cross-linking occurs that reduces enzyme activity.

In developing the data that is reproduced in FIG. 1 the consistent practice was to employ one volume of sedimented immobilized enzyme, on alkali-treated silica gel, with two volumes of the dialdehyde, at whatever concentration of dialdehyde was being used.

Glyoxal (ethanedial) is a superior cross-linker, although the reason for its better performance is not clear. Apparently, from the data plotted in FIG. 1, if the use of glyoxal in excess of that required for coupling leads to intra-layer cross-linking, then the reduction in enzyme activity is much less than is the case with the other dialdehydes.

The choice of cross-linking dialdehyde has some effect upon the way in which the enzyme performs. Thus, the optimum pH of lactase immobilized on silica gel in accordance with the invention is pH 6.75 when the cross-linker is glyoxal, and pH 6.50 when the cross-linker is glutaraldehyde, as compared to pH 7.0 for free lactase. These data suggest that the immobilized lactase retains a more active conformation when coupled with glyoxal than with glutaraldehyde. This comparative data was developed through performance evaluation of immobilized lactase on ONPG at 30° C.

The substrate selected also has a bearing on the performance of immobilized enzyme. Thus, when lactase is immobilized on alkali/acid activated silica gel, using glyoxal as the coupling agent, the immobilized enzyme generally performs better at a lower pH on lactose than on ONPG.

Immobilized lactase, on alkali/acid activated silica gel, ordinarily would be used for processing whey at a temperature of about 20° C. (room or ambient temperature) or less, and at the optimum pH for the particular lactase. Thus, for lactase from *Aspergillus niger*, a pH of about 4.5 would be best for enzyme efficiency.

In Table 2, the loss of lactase activity was observed when the immobilized lactase acted on ONPG as a substrate, at 50° C. At this temperature, which is well above the temperature at which the immobilized enzyme would ordinarily be used, the reaction goes forward rapidly, but the loss of enzyme activity is also rapid. The Table 2 data demonstrate that the loss in total activity is less for a double layer immobilized lactase than for a single layer, indicating that the enzyme has been stabilized by the immobilization procedure.

In Table 3, the units of enzyme activity per unit volume, at 30° C., are compared as between one, two and three layers, and where the coupling agent is glyoxal and glutaraldehyde. The figures for two layers and for three layers report the percentage increase in activity as compared to a single layer. The activity "density" for the three layer immobilized enzyme is very high, making this material very attractive for use in industrial processes.

Enzyme stability for lactase on silica gel at 50° C. on an ONPG substrate is reported in Table 4, and half-life is reported in Table 5. The three layer material clearly has been thermally stabilized to a very significant extent, and the half-life significantly extended.

From other experiments, it has been determined that beyond about 4 layers, the expense of multiple layering tends to offset the gains, possibly because some cross-linking between layers may occur. Generally, with lactase immobilized on alkali/acid activated silica gel, activity levels in the range from about 7.5 units/ml. to about 30 units/ml., on ONPG at 30° C., sedimented gel volume, are readily obtained. The lactase enzyme used in practising the invention may be from any desired source; that from *Saccharomyces fragilis* is suitable. When immobilized on alkali-treated silica gel with glyoxal, in two layers, a stability as to activity is ordinarily observed such that at least 20% of the initial activity persists after 7.5 minutes at 50° C. at a pH of about 6.7.

While the dialdehyde cross-linkers, and specifically glyoxal, represent preferred materials, the di-imidoesters and bis-imidates are also preferred materials. The imidoester dimethyl adipimidate approaches glyoxal in its performance as a coupling agent.

The enzymes suitable for immobilization are those having available amine groups. This includes most enzymes of proteinaceous nature. Lactase and glucose isomerase are commercially valuable enzymes that can be immobilized in single or multiple layers successfully. The same techniques described in Example 1 are useful for producing immobilized glucose isomerase in multiple layers. Immobilized glucose isomerase is especially useful for producing high fructose corn syrup, by reason of its high activity per unit volume.

Enzymes may be obtained from any suitable source, either vegetable, animal or microbiological. In addition to those mentioned above, the enzymes that act on starch and on sugars are of particular interest. Other enzymes that may be used in accordance with the invention include, for example, cellulase, esterase, nuclease, invertase, amyloglucosidase, and other types of hydrolases; hydrase, pectinases, pepsin, rennin, chymotrypsin, trypsin, urease, agrinase, lysozyme, cytochrome, 11-beta-hydroxylase, and mixtures of these and other enzymes.

In addition, other biologically active materials may be immobilized in single or multilayer fashion. The multilayer immobilized biologically active material thus obtained has a high level of activity per unit volume that makes the immobilized material very valuable for use in diagnostic assay applications, purification operations, and chromatography applications. For example, many antibodies and antigens have available amine groups. When an antibody or antigen is immobilized in accordance with the present invention, it provides a valuable means for isolating its complementary immunochemical reactant, offering potential for diagnostic assays.

Similarly, hormones having available amine groups may be immobilized in multiple layers to provide highly concentrated sources of hormone activity.

Among the features and advantages of the present invention are the high mechanical stability, the high thermal stability, and the high operational stability or halflife of the immobilized biologically active materials. In achieving some of these advantages and features, the selection of the crosslinking agent and the extent of cross-linking are important. Particularly outstanding is the performance of multiple layer immobilized enzyme as a catalyst for a variety of reactions for which enzymes are useful.

When the carrier is the preferred material, alkali/acid activated silica gel, the immobilized enzyme can conveniently be transferred from one container to another by pouring the particulate, free flowing particles, which act very much like a liquid. This facilitates use of the immobilized enzyme in conventional reactors such as, for example, pressure leaf filters and upright columns. When lactase is immobilized on silica gel in four layers, a good performance can be obtained in converting lactose to sweeter forms that are more readily assimilable, permitting use of the invention for the processing of milk, whey, and other dairy materials.

While the invention has been described in connection with specific embodiments thereof, it will be understood that it is capable of further modifications, and this application is intended to cover any variations, uses, or adaptations of the invention following in general the principles of the invention and including such departures from the present disclosure as come within known or customary practice within the art to which the invention pertains and as may be applied to the essential features hereinbefore set forth, and as fall within the scope of the appended claims.

We claim:

1. A process for producing a carrier for immobilization of enzyme material by reacting a particulate, finely divided siliceous inorganic carrier material to activate its surface areas with hydroxyl groups, comprising
   reacting the siliceous carrier material at a pH above 10 with a strongly basic solution in which said carrier material retains its particulate form, for a sufficient time to generate surface groups on the particles of the carrier material of the type Si-O$^-$M$^+$, where M is a metallic ion, an ammonium ion, or represents a mixture thereof, and then
   replacing the M$^+$ with H by reacting the carrier material with a strongly acid solution, so that the carrier surface has reactive hydroxyl groups disposed thereon.

2. The process of claim 1 wherein the siliceous inorganic carrier material is silica gel.

3. The process of claim 1 or 2 wherein the strongly basic solution is a solution of an alkali metal hydroxide having a concentration of at least 0.1% by weight, or the equivalent.

4. The process of claim 3 wherein the reaction temperature is at least 20° C.

5. The process of claim 4 wherein the reaction in the strongly basic solution is continued for at least 30 minutes.

6. The process of claim 5 wherein the strongly basic solution is an aqueous solution of an alkali metal hydroxide at a concentration up to about 5% by weight.

7. The process of claim 6 wherein the reaction time in the strongly basic solution is in the range from about 30 minutes to about 2 hours, after which the carrier material is treated with a strong acid to replace the $M^+$ with H.

8. The process of claim 7 wherein the acid is a mineral acid.

9. In a composite wherein an enzyme having available amine groups is immobilized to a siliceous inorganic carrier material by covalent bonding to hydroxyl groups pendant from the surface of the carrier material, the improvement wherein the carrier is a finely divided particulate siliceous inorganic carrier activated according to the process of claim 1.

10. The composite of claim 9 wherein the siliceous inorganic carrier material is a silica gel.

11. The composite of claim 10 wherein reaction with the strongly basic solution is carried out by reaction of the siliceous carrier with an aqueous solution of an alkali metal hydroxide at a pH of at least 11 at a temperature in the range from about 20° C. to about 45° C. for a period of time in the range from about 30 minutes to about 2 hours.

12. The composite of claim 11 wherein an organosilane is covalently bonded to hydroxyl groups on the surface of the activated carrier material, and the silane has pendant groups covalently bonded to said enzyme, which is immobilized thereby.

13. The composite of claim 12, wherein the enzyme is lactase.

14. A process for producing a carrier for immobilization of enzyme material by developing a high density of reactive hydroxyl groups on the surfaces of particles of finely divided silica gel, comprising
reacting silica gel with an aqueous solution of a strongly basic material selected from the group consisting of alkali metal hydroxides, alkali metal carbonates, and mixtures thereof, at a pH of at least about 10, at a temperature in the range from about 20° C. to about 45° C., for a period of time from about 30 minutes to about 2 hours, during which reaction the silica gel retains its particulate form,
separating the alkali-reacted, particulate silica gel from the basic solution, and then
reacting the said alkali-reacted, silica gel particles with a strong aqueous solution of mineral acid to remove metal ion from the gel and to activate the gel surfaces with reactive hydroxyl groups.

15. The process of claim 14 wherein the pH of the strongly basic solution is at least 11.

16. A process for immobilizing an active enzyme material having available amine groups, at a high density of immobilization per unit volume, comprising
reacting a finely divided particulate silica gel carrier, that has been activated by the process of claim 14, with a polyvalent covalent coupling agent, to immobilize the coupling agent to the activated silica gel, then
removing excess coupling agent, then
reacting the active enzyme material with the immobilized coupling agent, to immobilize the active enzyme material to the silica gel particles.

17. The process of claim 16 wherein the coupling agent is selected from the group consisting of an aminosilane and cyanogen bromide.

18. The process of claim 17 wherein the coupling agent is an aminosilane and the aminosilane is gamma-aminopropyltriethoxysilane, and the enzyme is lactase.

19. In a reactive composite comprising an activated silica gel carrier, a first enzyme immobilized to the carrier through a chemical bond to reactive hydroxyl groups of the carrier, said enzyme retaining its activity, and at least one additional amount of enzyme immobilized to said first enzyme by a chemically bonded link between said enzymes, said additional amount of enzyme retaining its activity, the improvement wherein the carrier is a silica gel activated by the process of claim 14 to contain reactive hydroxyl groups on the surface of the carrier to have a greater amount of said first, enzyme immobilized thereto than if not so activated.

20. In an immobilized enzyme composite comprising a carrier of solid, free-flowing particles, a first amount of enzyme immobilized to the carrier, and a second amount of enzyme immobilized by covalent coupling through a divalent coupling agent to said first-named enzyme, substantially all of said enzyme retaining characteristic activity, the improvement wherein said first amount of enzyme is immobilized to the carrier by the process of claim 17.

21. The composite of claim 20 wherein said first-named enzyme and said second-named enzyme are the same enzyme.

22. The composite of claim 21 wherein said first-named enzyme and said second named enzyme are lactase.

* * * * *

UNITED STATES PATENT AND TRADEMARK OFFICE
CERTIFICATE OF CORRECTION

PATENT NO. : 4,384,045
DATED : May 17, 1983
INVENTOR(S) : Guan-Huei HO and Chiang-Chang-LIAO It is certified that error appears in the above—identified patent and that said Letters Patent is hereby corrected as shown below:

Cover page, line [73] Assignee; "Borden, Inc., Columbus, Ohio" should be: The Borden Company Limited, Ontario, Canada Signed and Sealed this Twenty-seventh Day of December 1983

[SEAL]

Attest:

GERALD J. MOSSINGHOFF

Attesting Officer  Commissioner of Patents and Trademarks